United States Patent

Hargest

[11] Patent Number: 5,206,896
[45] Date of Patent: Apr. 27, 1993

[54] IMMOBILIZATION OF DOMESTIC ANIMALS IN A BED OF FLUIDIZABLE SOLID PARTICLES

[76] Inventor: Thomas S. Hargest, P.O. Box 21118, Charleston, S.C. 29413

[21] Appl. No.: 808,011

[22] Filed: Dec. 13, 1991

[51] Int. Cl.⁵ .................. H05G 1/00; G03B 42/02
[52] U.S. Cl. ....................... 378/180; 378/208; 128/24.1; 128/38; 5/912
[58] Field of Search ............ 378/80, 208, 180; 128/24.1, 38, 65; 5/912

[56] References Cited

U.S. PATENT DOCUMENTS

| Re. 31,866 | 4/1985 | Lines et al. | 128/419 |
|---|---|---|---|
| 3,760,800 | 9/1973 | Staffin et al. | 128/24.1 |
| 3,866,606 | 2/1975 | Hargest | 128/71 |
| 4,240,437 | 12/1980 | Church | 128/420 |
| 4,498,462 | 2/1985 | Henley | 128/24.1 |
| 4,541,418 | 9/1985 | Kirby | 128/24.1 |
| 4,583,530 | 4/1986 | Henley | 128/65 |
| 4,648,392 | 3/1987 | Cartier et al. | 128/160 |

FOREIGN PATENT DOCUMENTS 332242A of 0000 European Pat. Off. .

Primary Examiner—Paul M. Dzierzynski
Assistant Examiner—Kim-Kwok Chu
Attorney, Agent, or Firm—Luke J. Wilburn, Jr.

[57] ABSTRACT

Method and apparatus for immobilizing at least a portion of a domestic animal for treatment in which the portion of the animal is submerged in a fluidized bed of solid particles, and the bed de-fluidized to immobilize the portion of the domestic animal for a desired period of time. The invention may be employed to immobilize a large domestic animal, such as a horse, up to the chest of the animal, for post-operative care, and to immobilize a body portion of an animal, such the leg, for purposes of X-ray photography.

10 Claims, 2 Drawing Sheets

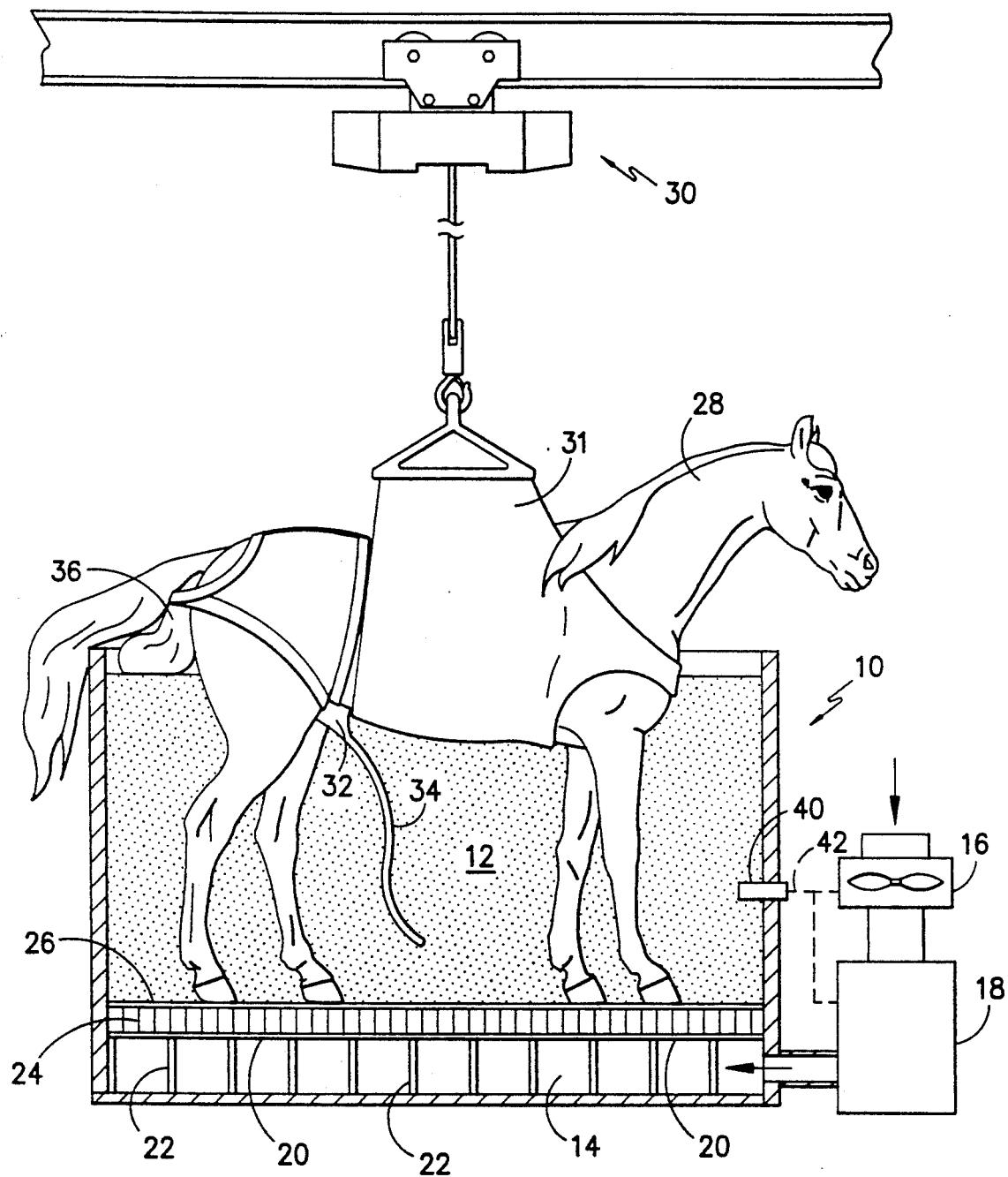
FIG. —1—

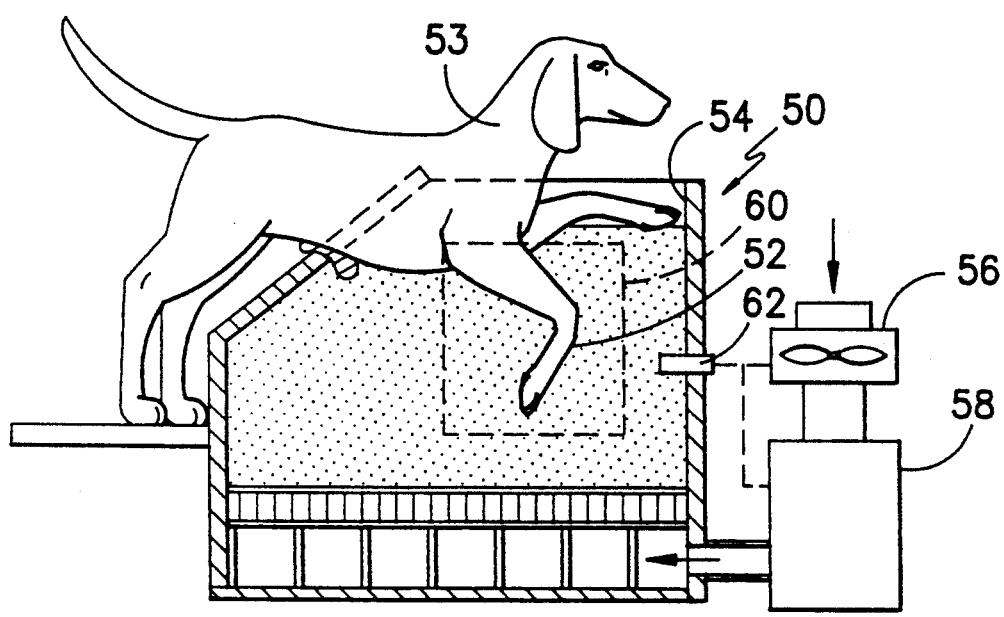
FIG. -2-

IMMOBILIZATION OF DOMESTIC ANIMALS IN A BED OF FLUIDIZABLE SOLID PARTICLES

This invention relates to method and apparatus for immobilizing at least a portion of a domestic animal for treatment, and, more particularly, to method and apparatus for immobilizing a body portion of a domestic animal, such as post-operative immobilization of the animal or immobilization of a leg of the animal for X-ray, and the like.

BACKGROUND OF THE INVENTION

In animal husbandry it is often desirable to immobilize a large domestic animal for operatory veterinary procedures of for post-operative care. In operatory veterinary procedures, the animal may be anesthetized by administration of a drug; however, for short non-invasive procedures, such as to X-ray the leg of an animal, or in longer procedures, such as post-operative recovery when it is desirable that the animal be maintained in a fixed position to permit healing and cure, the use of drugs and anesthetics is impractical.

U.S. Pat. No. Re. 31,866 discloses method and apparatus for temporarily immobilizing a domestic animal without rendering the animal unconscious by passing a pulsed electric current through the animal's muscles to cause a state of tetany in the muscles while leaving the organs in a relaxed condition.

It has been suggested in treatment of large domestic animals to employ fluidized beds of solid particulate material for massage and thermal therapy. U.S. Pat. No. 4,583,530 discloses method and apparatus for equine therapy by immersing two legs of a horse in a fluidized bed of solid particles which may be heated or cooled for treatment of pain, blood flow insufficiency, and post-operative muscle, tendon, and nerve repair.

European Patent Application 332,242-A discloses the use of a fluidized bed of absorbing beads for abstracting moisture and fluid from various bodies, such as industrial and agricultural products, humans, and animals, wherein the fluidized beads of the bed are maintained at a relative degree of humidity and suitable temperature to abstract moisture from the bodies.

U.S. Pat. No. 4,498,462 discloses apparatus for therapeutic massage of parts of the body of humans or animals utilizing a fluidized solids bed as a heat transfer medium.

U.S. Pat. No. 4,240,437 discloses method and apparatus for treating animals with pulsating electrical potential applied across electrodes placed on the animals.

U.S. Pat. No. 4,648,392 discloses apparatus for treating oedema of members of the body such as the leg of a human wherein the leg to be treated is introduced into a flexible bag and mercury introduced into space surrounding the bag. The fluidized bed surrounding the body member in the mercury is de-fluidized to form a solid molding around the leg and mercury during treatment.

U.S. Pat. No. 3,866,606 discloses apparatus and method for cyclically forming a precisely contoured support for a patient requiring a fixed position, as for example, undergoing traction, by means of periodically fluidizing granular material disposed within a container which, upon successive fluidization, forms the contoured support to distribute pressure over a substantial portion of the body of a patient in avoidance of concentrated pressure on restricted areas thereof.

BRIEF OBJECTS OF THE PRESENT INVENTION

It is an object of the present invention to provide method and apparatus for immobilizing at least a portion of a domestic animal for treatment, such as in post-operative immobilization of the animal, without the use of anesthetic or drug therapy which would render the animal unconscious.

It is another object to provide method and apparatus for immobilizing the leg of a domestic animal for X-ray photography.

It is a more specific object to provide method and apparatus for immobilizing at least a portion of a large domestic animal for extended periods of time after surgical procedures, such as repair of a broken or fractured leg, while maintaining the animal conscious and with otherwise normal body functions.

SUMMARY OF THE INVENTION

This invention comprises method and apparatus for immobilizing a least a portion of a domestic animal for animal husbandry or veterinary treatment wherein at least a portion of the body of the animal is submerged in a fluidized bed of solid particles, and the bed is de-fluidized to immobilize the portion of the animal in the solid particles for a desired period of time. After treatment, the bed is re-fluidized and the body portion of the animal may be removed from the fluidized bed.

In one embodiment, the method and apparatus of the present invention includes means for immobilizing the four legs of a large domestic animal submerged in a fluidizable bed up to about the chest of the animal, with means provided for collecting body waste products from the animal.

In another embodiment, method and apparatus are provided for immobilizing the leg of an animal in a fluidizable bed of solid particles having X-ray transparency to permit X-ray photography of the leg.

BRIEF DESCRIPTION OF THE DRAWINGS

The above, as well as other objects of the present invention, will become more apparent and the invention will be better understood from the following detailed description of preferred embodiments of the invention, when taken together with the accompanying drawings, in which:

FIG. 1 is a diagrammatic reproduction, with certain components shown in vertical section, of apparatus of the invention for immobilizing a large domestic animal for extended periods of time, such as in post-operative care, to permit healing and cure of the animal;

FIG. 2 is a sectional elevation view of another embodiment of apparatus for immobilizing at least a portion of a domestic animal, such as the foreleg of a dog, for X-ray photography and treatment.

DETAILED DESCRIPTION OF PREFERRED EMBODIMENTS OF THE INVENTION

As best seen in FIG. 1, the apparatus of the present invention for carrying out the method of the present invention may comprise a large container, or tank, 10, which may be of rectangular horizontal cross-section, for receiving a mass of solid particulate material, such as glass beads 12, or the like. The tank includes an air plenum, or compartment, 14, in the bottom of the tank which receives temperature-controlled, pressurized air from a heated or cooled pressurized air source, such as a compressor or air blower 16 with suitable heating and cooling unit, such as a heat pump, 18. The air plenum 14 includes a horizontal expanded metal support member 20 reinforced by plurality of vertical support members 22. Located on support member 20 is a perforated air diffuser board 24 having a plurality of openings therethrough for the passage of pressurized air from plenum 14 up into the fluidizable bed of glass beads.

Positioned above diffuser board 24 is an expanded metal protective floor 26 secured to side walls of tank 10. Floor 26 is of sufficient strength to support the weight of a large domestic animal, such as a horse 28, in standing position in the tank.

The apparatus shown in FIG. 1 may be employed to immobilize a large domestic animal, such as the horse 28, for extended periods of time, as after leg surgery or fracture repair. The horse 28, generally in sedated condition, is lifted by means of a movable hoist device 30 with sling 31 into the fluidizable bed as air is directed into the bed under sufficient pressure to fluidize the same. As illustrated, the horse 28 is placed in an upright standing position with the bed fluidized to cover the horse up to its chest area. A urine collection device 32 attached to the horse by suitable means, such as an adhesive or strap connections, directs collected urine by means of a tube 34 to a waste collection point outside the tank 10. Similarly, fecal waste is collected by means of a bag collector 36 located adjacent the upper edge of the fluidized bed and attached to the horse by suitable means, such as straps.

After placement of the horse in standing position in the fluidized bed, the hoist device 30 is removed from the sling 31 and the pressurized air is reduced, or cut off, to de-fluidize the bed of glass beads, thus firmly encasing the legs and lower body portion of the horse therein to immobilize the same. Periodically, heated or cooled air from blower 16 and heat pump 18 may be passed through the de-fluidized bed to maintain temperature control of the bed during immobilization of the horse. Temperature sensing and control means, such as a thermostat device 40 with conventional automatic or manual control 42, may be electrically connected, in conventional manner, to operate blower 16 and heat pump 18 at a desired air pressure and temperature, respectively.

To remove the horse from the fluidized bed, the de-fluidized bed is re-fluidized by pressurized air, and the hoist 30 and sling 31 is employed to lift and remove the horse from the fluidized mass of beads.

In the embodiment of the invention shown in FIG. 2, a smaller fluidized bed container 50 of a type as generally described in FIG. 1 is sized to receive a leg 52 of a domestic animal, shown as a dog 53, therein. Side walls 54 of the container 50 are composed of X-ray transmissible material, such as a suitable plastic. The bed may be fluidized by pressurized air from blower unit 56. A heat pump 58 may be provided, if desired, for control of bed temperature. When the fluidized bed of glass beads containing the leg 52 of the animal is defluidized to immobilize the leg, X-ray equipment may be employed to photograph the leg on an X-ray film and plate 60 suitable supported on the rear wall of container 50. Re-fluidizing the bed permits removal of the leg of the animal after X-ray treatment. Operation of the blower unit 56 and heat pump 58 for fluidization and thermal control of the bed may be by thermostat and blower unit controls suitably located as at 62.

That which is claimed is:

1. A method of immobilizing at least a portion of a domestic animal for treatment, comprising the steps of
   (a) creating a fluidized bed of solid particles,
   (b) submerging at least a portion of the body of a domestic animal in the fluidized bed,
   (c) de-fluidizing the bed of solid particles to immobilize said portion of the animal in the solid particles for a desired period of time,
   (d) re-fluidizing the bed of solid particles, and
   (e) removing said portion of the body of the animal from the fluidized bed.

2. A method as defined in claim 1 wherein four legs of the animal are submerged in the fluidized bed with the animal in an upright, standing position during immobilization.

3. A method as defined in claim 2 wherein the four legs of the animal are submerged in the fluidized bed up to about the chest of the animal and including the steps of collecting body waste products from the animal while immobilized in the fluidized bed and directing them to a waste collection point.

4. A method as defined in claim 1 wherein the de-fluidized bed of solid particles is transmissible to X-ray, and including the step of conducting X-ray photography of a portion of the body of the animal during immobilization of the portion in the solid particles of the de-fluidized bed.

5. A method as defined in claim 4 wherein the portion of the body of the animal immobilized in the solid particles is a leg portion of the animal.

6. A method as defined in claim 1 including the steps of controlling the temperature of the de-fluidized bed of solid particles during immobilization of the portion of the animal therein.

7. Apparatus for immobilizing at least a portion of a domestic animal for treatment, comprising means for creating a fluidized bed of solid particles of sufficient size to submerge at least a portion of the body of a domestic animal therein, means for de-fluidizing the bed of solid particles to immobilize the portion of the animal in the solid particles for desired period of time, means for re-fluidizing the bed of solid particles, and means for removing a portion of body of the animal from the fluidized bed.

8. Apparatus as defined in claim 7 wherein the means for creating a fluidized bed of solid particles is of sufficient size to submerge four legs of a domestic animal in the fluidized bed with the animal in upright, standing position during immobilization.

9. Apparatus as defined in claim 8 wherein the means for creating a fluidized bed of solid particles is of sufficient size to submerge the animal in the fluidized bed up to about the chest of the animal, and means for collecting body waste products from the animal while immobilized in the fluidized bed and directing them to a waste collection point.

10. Apparatus as defined in claim 7 wherein the means for creating the fluidized bed of solid particles is X-ray transmissible to permit X-ray photography of the portion of the body of the animal therein during immobilization in the solid particles of the de-fluidized bed.

* * * * *